US008915856B2

(12) United States Patent
Yang et al.

(10) Patent No.: US 8,915,856 B2
(45) Date of Patent: Dec. 23, 2014

(54) ULTRASONIC DIAGNOSTIC APPARATUS WITH IMAGE FILTERING BASED ON BLOOD FLOW INFORMATION

(75) Inventors: Eun Ho Yang, Seoul (KR); Mi Jeoung Ahn, Seoul (KR); Chul An Kim, Gyeonggi-do (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 189 days.

(21) Appl. No.: 12/961,223

(22) Filed: Dec. 6, 2010

(65) Prior Publication Data

US 2011/0137170 A1    Jun. 9, 2011

(30) Foreign Application Priority Data

Dec. 7, 2009    (KR) .................... 10-2009-0120444

(51) Int. Cl.
*A61B 8/00*   (2006.01)
*G06T 7/00*   (2006.01)
*G01S 15/89*  (2006.01)
*G06T 5/00*   (2006.01)
*A61B 8/06*   (2006.01)

(52) U.S. Cl.
CPC ....... *G06T 5/002* (2013.01); *G06T 2207/30104* (2013.01); *G06T 2207/10132* (2013.01); *G06T 7/0012* (2013.01); *G01S 7/0012* (2013.01); *G01S 15/8979* (2013.01); *G06T 2207/20012* (2013.01); *A61B 8/06* (2013.01)
USPC ............................ 600/454; 600/441; 382/128

(58) Field of Classification Search
USPC ......... 600/407, 437, 438, 440, 441, 443, 446, 600/450, 453, 454, 455, 456, 457, 458
See application file for complete search history.

(56) References Cited

U.S. PATENT DOCUMENTS

| 5,215,093 A * | 6/1993 | Miyazaki et al. ............. 600/455 |
| 5,921,931 A * | 7/1999 | O'Donnell et al. ........... 600/441 |
| 2003/0097068 A1 | 5/2003 | Hossack et al. |
| 2005/0053305 A1 | 3/2005 | Li et al. |
| 2006/0116578 A1 * | 6/2006 | Grunwald et al. ............ 600/440 |
| 2008/0077010 A1 * | 3/2008 | Cohen-Solal et al. ........ 600/441 |
| 2010/0280383 A1 * | 11/2010 | Kim et al. ..................... 600/453 |

FOREIGN PATENT DOCUMENTS

| EP | 1 684 232 A1 | 7/2006 |
| JP | 2008-154891 A | 7/2008 |
| KR | 10-0760251 B1 | 9/2007 |

OTHER PUBLICATIONS

European Search Report issued in European Patent Application No. 10189400.4-2218, mailed Mar. 11, 2011.

(Continued)

*Primary Examiner* — Unsu Jung
*Assistant Examiner* — Amanda Lauritzen
(74) *Attorney, Agent, or Firm* — McDermott Will & Emery LLP

(57) ABSTRACT

The present disclosure relates to an ultrasonic diagnostic apparatus. The ultrasonic diagnostic apparatus transmits an ultrasound signal to a diagnosis target and receives the reflected ultrasound signal from the diagnosis target to generate an ultrasound image. The ultrasound image to be displayed on a screen is divided into plural division regions, and filtering is performed for the respective division regions based on blood-flow information at plural division positions on the diagnosis target corresponding to the respective division regions to provide the filtered result as the ultrasound image.

8 Claims, 4 Drawing Sheets

(56) References Cited

OTHER PUBLICATIONS

Frangi, A., et al., "Multiscale Vessel Enhancement Filtering", Jan. 1998, pp. 130-137, vol. 1496, Springer-Verlag, Berlin Heidelberg.

Suri, J., et al., "A Review on MR Vascular Image Processing Algorithms: Acquisition and Prefiltering: Part 1", IEEE Transactions on Information Technology in Biomedicine, Dec. 2002, pp. 324-337, vol. 6 No. 4.

Korean Office Action issued in Korean Patent Application No. KR 10-2009-0120444 dated Mar. 29, 2011.

\* cited by examiner

Fig. 4

| A1 | A2 | A3 |
|----|----|----|
| A4 | A5 | A6 |
| A7 | A8 | A9 |

ULTRASONIC DIAGNOSTIC APPARATUS WITH IMAGE FILTERING BASED ON BLOOD FLOW INFORMATION

BACKGROUND OF THE INVENTION

1. Field of the Invention

The present invention relates to an ultrasonic diagnostic apparatus and, more particularly, to an ultrasonic diagnostic apparatus that provides an ultrasound image having improved image quality through efficient filtering and image synthesis.

2. Description of the Related Art

An ultrasonic diagnostic apparatus has non-invasive and non-destructive characteristics, and is thus widely used in a medical field to obtain information about the interior of a diagnosis target. The ultrasonic diagnostic apparatus can provide a real-time high-definition image of internal tissue of a human body to a doctor without surgical operation entailing direct incision and observation of the human body, and is thus very important in the field of medicine.

The ultrasonic diagnostic apparatus electrically stimulates conversion elements to generate an ultrasound signal and transmits the generated ultrasound signal to a human body. The ultrasound signal is reflected as an ultrasound echo-signal at a boundary between discontinuous human tissues, and the ultrasound echo-signal transmitted to the conversion elements from the boundary between the human tissues is converted into an electrical signal. The ultrasonic diagnostic apparatus amplifies and signal-processes the converted electrical signal to generate ultrasound image data about the human tissue.

Generally, the ultrasonic diagnostic apparatus performs filtering of ultrasound image data using a filtering mask to remove various noise and obtain a clear image when forming the ultrasound image of each part of the body.

Meanwhile, conventional ultrasonic diagnostic apparatuses have a specific kind of filtering mask defined for use with each part of the body, for example, the liver, kidney, pancreas, heart, and the like. Accordingly, in the case of the kidney, the conventional ultrasonic diagnostic apparatus performs filtering upon ultrasound image data of the kidney using a single pre-designated filtering mask so as to obtain an overall ultrasound image of the kidney, as shown in a right side of FIG. 1. For reference, FIG. 1 comparatively shows a schematic diagram (left side) of an actual kidney and an ultrasound image (right side) of the kidney generated by the conventional ultrasonic diagnostic apparatus.

Conventionally, since filtering is performed corresponding to a blood vessel having a size of a specific range, as shown in the right side of FIG. 1, it is possible to obtain a relatively clear image of the blood vessel having a size or thickness greater than a certain value in the generated ultrasound image, but the filtering is not appropriately achieved for a blood vessel having a size or thickness smaller than the certain value, causing several small blood vessels adjacent to each other to be displayed in a superimposed state, so that the small blood vessels are not clearly displayed individually.

That is, the conventional ultrasonic diagnostic apparatus provides a mixed image of a clearly displayed portion and an unclearly displayed portion depending on the size or position of each of the body parts, particularly, the blood vessel, and the like. In order to make the unclearly displayed portion clear, there is an inconvenience to reset the filtering mask so as to match with the size of the blood vessel, and the like. Furthermore, in such a case, there is a problem that the existing clearly displayed portion is not appropriately filtered and becomes unclear.

SUMMARY OF THE INVENTION

An aspect of the present invention is to provide an ultrasonic diagnostic apparatus capable of obtaining a clear ultrasound image regardless of a size or position of each body part, particularly, a blood vessel, and the like.

In accordance with one aspect of the invention, an ultrasonic diagnostic apparatus transmitting an ultrasound signal to a diagnosis target and receiving a reflected ultrasound signal from the diagnosis target to generate an ultrasound image is provided, wherein the ultrasound image to be displayed on a screen is divided into plural division regions, and filtering is performed for the respective division regions based on blood-flow information at plural division positions of the diagnosis target corresponding to the respective division regions to provide a filtered result as the ultrasound image.

The ultrasonic diagnostic apparatus may include a probe; a beam former; a signal processor signal-processing frame data generated by the beam former to generate ultrasound image data and obtaining the blood-flow information at the plural division positions on the diagnosis target; a matching unit determining filtering masks corresponding to each of the division positions respectively based on the blood-flow information at each of the obtained division positions; a filtering unit filtering the ultrasound image data using the determined filtering masks to generate filtered ultrasound image data; a synthesizer synthesizing the filtered ultrasound image data to form the ultrasound image; and a display unit.

The synthesizer may acquire plural division images corresponding to the division positions respectively from each of the filtered ultrasound image data and synthesize the division images.

The synthesizer may include division-image acquisition units each acquiring the division image corresponding to the respective desired division position from the respective filtered ultrasound image data; and an image allocation unit allocating the plural division images, provided from the division-image acquisition units, to the corresponding division regions on the screen, respectively.

The blood-flow information may include at least one of blood flow-rate information, blood vessel thickness information, blood vessel direction information, blood flow intensity, and blood flow volume.

The blood flow-rate information may be obtained by Doppler information based on the ultrasound signal.

The division positions may be set in a preset unit of a certain number of plural pixels on the screen.

The preset unit of a certain number of plural pixels may be set by a user.

The ultrasound image to be displayed on the screen may be divided into a predetermined number of the division regions each having the same size, and the division positions may be set corresponding to the division regions, respectively.

The predetermined number of division regions may be set by a user.

The ultrasound image may allow conversion into a three-dimensional image.

When at least one region of interest (ROI) is set by a user, filtering may be performed only for the at least one region of interest.

BRIEF DESCRIPTION OF THE DRAWING

The above and other aspects, features and advantages of the invention will become apparent from the following detailed description in conjunction with the accompanying drawing, in which:

FIG. 4 shows one example of an ultrasound image divisionally displayed on a screen of a display unit of the ultrasonic diagnostic apparatus according to the embodiment.

DETAILED DESCRIPTION OF THE EMBODIMENTS

Embodiments of the invention will now be described in detail. The embodiments are given by way of illustration only, and the scope of the invention is not limited by the embodiments.

Figure 1:
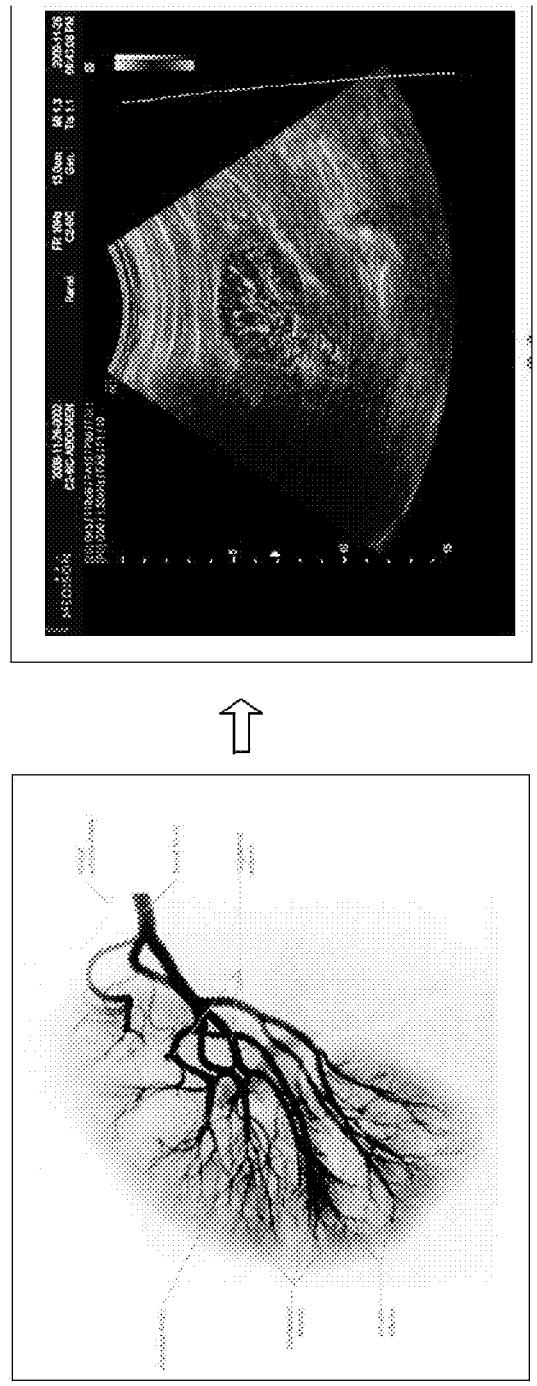
FIG. 1 comparatively shows a schematic diagram of an actual kidney and an ultrasound image of the kidney generated by a conventional ultrasonic diagnostic apparatus.
Figure 2:
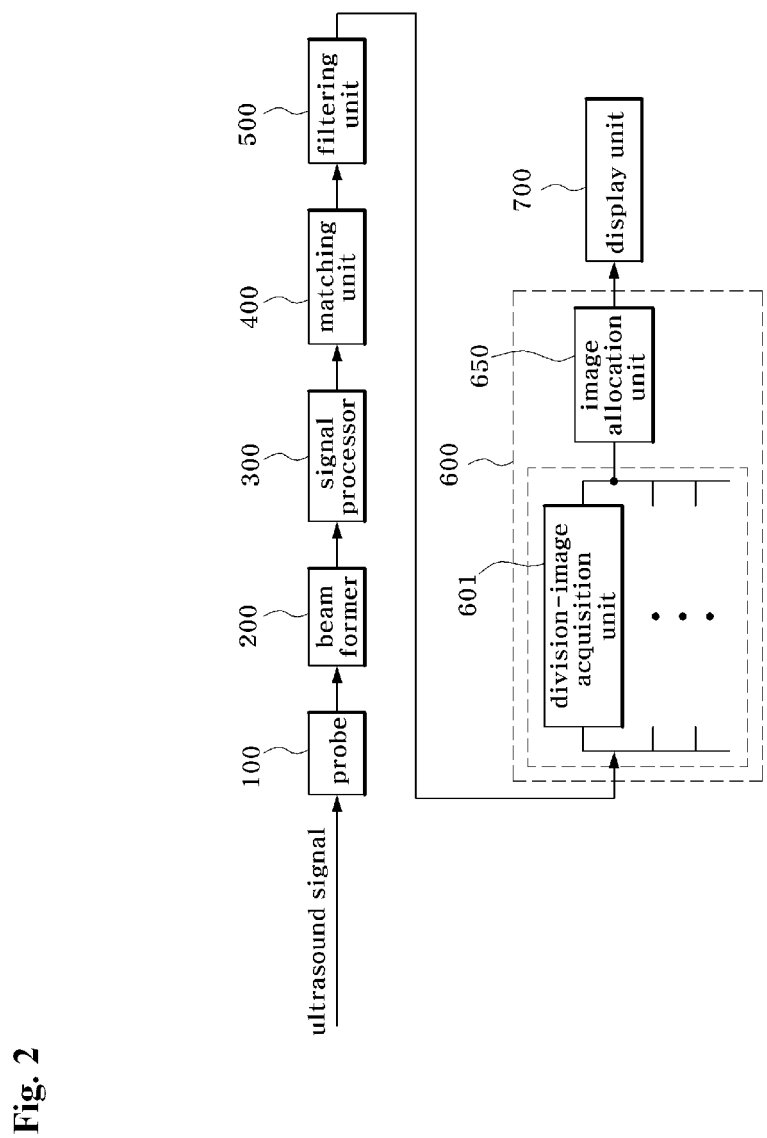
FIG. 2 is a block diagram of an ultrasonic diagnostic apparatus according to one embodiment of the present invention.
Figure 3:
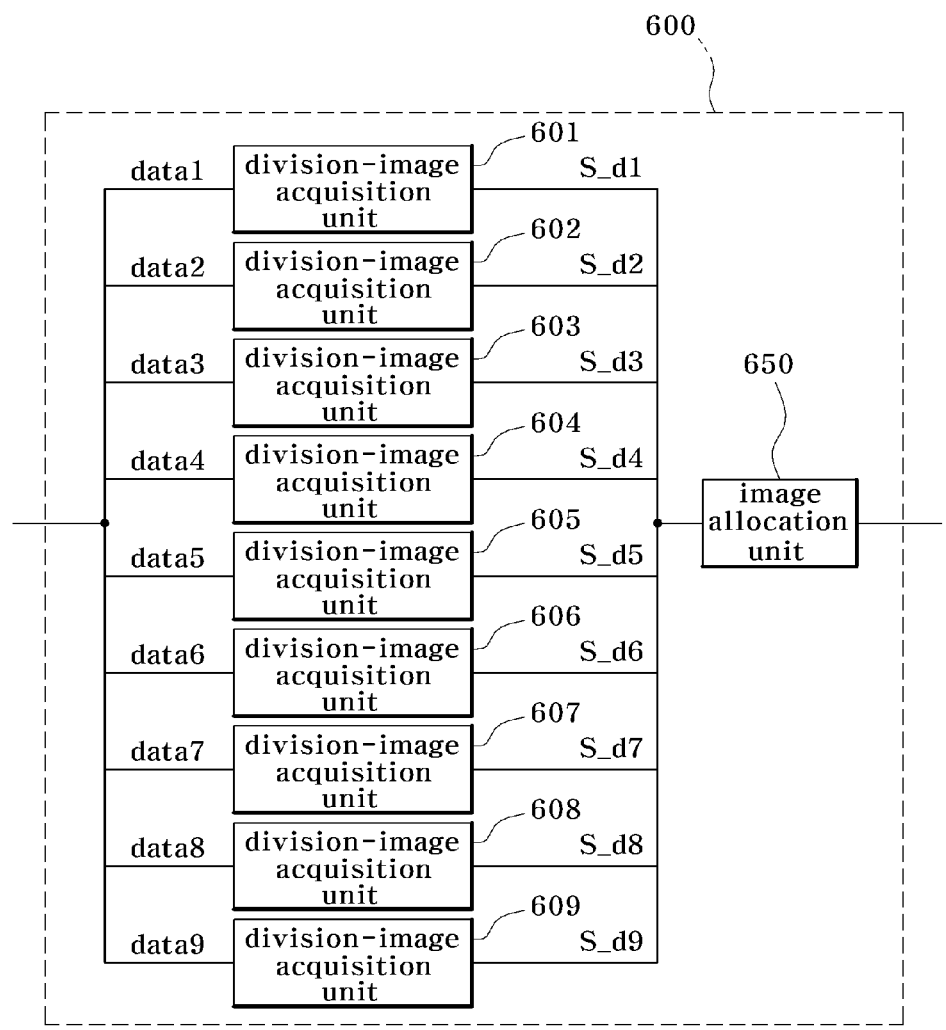
FIG. 3 is a block diagram of a synthesizer of the ultrasonic diagnostic apparatus according to the embodiment of the present invention.
Figure 4:
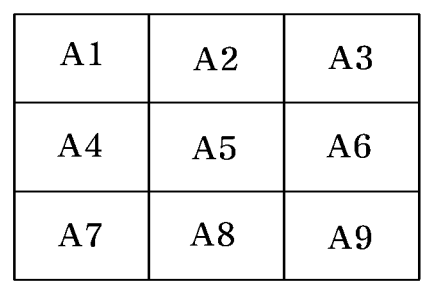

FIG. 2 is a block diagram of an ultrasonic diagnostic apparatus according to one embodiment of the invention, FIG. 3 is a block diagram of a synthesizer of the ultrasonic diagnostic apparatus, and FIG. 4 shows one example of an ultrasound image divisionally displayed on a screen of a display unit of the ultrasonic diagnostic apparatus. The invention will now be described with reference to these drawings.

Referring to FIG. 2, the ultrasonic diagnostic apparatus includes a probe 100 which transmits an ultrasound signal to a diagnosis target and receives a reflected ultrasound signal from the diagnosis target; a beam former 200 which collects the reflected ultrasound signal received by the probe 100 and generates frame data corresponding to the reflected ultrasound signal; a signal processor 300 which signal-processes the frame data to generate ultrasound image data and obtains blood-flow information at plural division positions on the diagnosis target; a matching unit 400 which determines filtering masks corresponding to each of the division positions respectively based on the blood-flow information at each of the obtained division positions; a filtering unit 500 which filters the ultrasound image data using the determined filtering masks to generate filtered ultrasound image data; a synthesizer 600 which synthesizes the filtered ultrasound image data to form the ultrasound image; and a display unit 700 which displays the ultrasound image.

The probe 100 includes a transducer array to transmit an ultrasound signal to a diagnosis target, for example, the liver, kidney, pancreas, heart, or the like, and to receive the ultrasound signal reflected from the diagnosis target.

The beam former 200 converges the ultrasound signal received by each of the transducer array elements of the probe 100 to generate frame data corresponding thereto.

Then, the signal processor 300 processes the frame data into a digital signal to generate ultrasound image data. Further, the signal processor 300 includes a frame buffer (not shown) and forms Doppler information including a number of blood flow rate information at each of the division positions on the diagnosis target based on the received ultrasound signal. The signal processor 300 obtains blood-flow information at the plural division positions using the Doppler information. Here, the blood-flow information may include at least one of blood flow rate information, blood vessel thickness information, blood vessel direction information, blood flow intensity, and blood flow volume. The blood-flow information including the blood flow rate information may be obtained by the Doppler information based on the ultrasound signal and various application techniques widely applied to the existing ultrasonic diagnostic apparatus. The ultrasound image data processed by the signal processor 300 may be two or three-dimensional image data, and are not limited to any one of them.

The plural division positions on the diagnosis target may be set in a preset area unit or in a preset unit of plural pixels on the screen. That is, assuming that an ultrasound image to be displayed on the screen of the display unit 700 is divided in a desired preset area unit or in a preset area unit corresponding to a certain number of plural pixels, the plural division positions on the diagnosis target may be set corresponding to the division regions, respectively. Further, in other embodiments, the ultrasound image to be displayed on the screen may be divided into a preset number of division regions (for example, nine, sixteen, . . . ) each having the same size, as shown in FIG. 4, and each of the division positions may be set corresponding to each of the division regions. Here, the desired preset area unit, the preset area unit corresponding to the certain number of plural pixels, the desired preset number of the division regions, and the like may be set automatically by a system or arbitrarily set by a user. To obtain a clearer ultrasound image, a method of making the size of each division region small or increasing the number of division regions may be applied.

Next, the matching unit 400 determines one of more filtering masks corresponding to each of the division positions respectively based on the blood-flow information at each of the obtained division positions. That is, since the size or thickness of a blood vessel and the like at each of the division positions constituting the diagnosis target is different from those at other division positions, different filtering masks are to be applied to the respective division positions to obtain clear ultrasound images at the respective division positions. The matching unit 400 serves to determine filtering masks suitable for each of the division positions respectively. For example, the matching unit 400 determines to apply a first filtering mask to a first division position based on blood-flow information at the first division position, and to apply a second filtering mask to a second division position based on blood-flow information at the second division position, and the like.

The filtering unit 500 filters ultrasound image data using the filtering masks determined by the matching unit to generate filtered ultrasound image data. That is, for example, when nine division regions are set on the screen, as shown in FIG. 4, nine division positions will be set for the nine division regions, respectively, and filtering masks suitable for each of the nine division positions will be determined by the matching unit 400, respectively. Then, the filtering unit 500 will apply each of the filtering masks to the ultrasound image data to generate nine filtered ultrasound image data (data1 to data9), as shown in FIG. 3. By doing this, first filtered ultrasound image data (data1) represents a filtered image suitable for the first division position, second filtered ultrasound image data (data2) represents a filtered image suitable for the second division position, and so forth. As such, each of the filtered ultrasound image data may be realized by a clear image for each of the corresponding division positions. Here, it should be understood that the number of division positions may be set differently in a differently preset area unit or in a differently preset unit of a certain number of plural pixels.

The synthesizer 600 synthesizes the filtered ultrasound image data to form an ultrasound image to be displayed on the display unit 700. Specifically, referring to FIG. 3, the synthesizer 600 includes division-image acquisition units 601 to 609 which acquire division images s_d1 to s_d9 corresponding to desired division positions (first to ninth division positions) from the respective filtered ultrasound image data (data1 to data9), and an image allocation unit 650 which allocates the division images s_d1 to s_d9, provided from the division-image acquisition units 601 to 609, to the corresponding division regions A1 to A9, respectively, on the screen.

That is, the division-image acquisition unit 601 acquires the division image s_d1 for the division position corresponding to the division region A1 on the screen of FIG. 4 and provides the division image s_d1 to the image allocation unit 650, the division-image acquisition unit 602 acquires the division image s_d2 for the division position corresponding to the division region A2 on the screen of FIG. 4 and provides the division image s_d2 to the image allocation unit 650, and so forth. As such, the division-image acquisition units 601 to 609 acquire the division images s_d1 to s_d9 for the respective division positions to be displayed in the respective division regions A1 to A9 on the screen and provide the division images s_d1 to s_d9 to the image allocation unit 650. Then, the image allocation unit 650 allocates the division image s_d1 to the corresponding division region A1 on the screen, the division image s_d2 to the corresponding division region A2 on the screen, and the like. As such, the division images s_d1 to s_d9 are allocated to the corresponding division regions A1 to A9, respectively.

The display unit 700 displays the ultrasound image synthesized by the synthesizer 600 on the screen. As such, the ultrasound image displayed on the screen has been filtered suitably for each of the division positions, so that the image is clearly displayed on the display unit 700 regardless of the position, thickness, size, and the like of a certain blood vessel at each of the division positions.

On the other hand, if the ultrasound image displayed on the display unit 700 is a two-dimensional image, it is possible to convert the two-dimensional image into a three-dimensional image using a three-dimensional image synthesis technique of any available ultrasonic diagnostic apparatus. Further, according to one embodiment, when plural regions of interest (ROI) are set by a user, the filtering process as described above may be performed for plural division positions corresponding to the regions of interest to efficiently obtain clear ultrasound images of the regions of interest.

Furthermore, in the above embodiments, filtering is performed using filtering masks suitable for ultrasound image data to obtain filtered ultrasound image data, which in turn are used to obtain division images for respective division positions, followed by synthesis of the division images. However, in another embodiment, the division images may be obtained by dividing, for each of the division positions, the ultrasound image data provided from the signal processor 300, and subjected to filtering through filtering masks suitable for each of the division images, followed by synthesis of the filtered division images to obtain a final ultrasound image.

As apparent from the above description, according to the embodiments, the ultrasonic diagnostic apparatus provides an ultrasound image having improved image quality through efficient filtering and image synthesis.

Although some embodiments have been provided to illustrate the invention in conjunction with the drawings, it will be apparent to those skilled in the art that the embodiments are given by way of illustration only, and that various modifications, changes, alterations, and equivalent embodiments can be made without departing from the spirit and scope of the invention. The scope of the invention should be limited only by the accompanying claims.

What is claimed is:

1. An ultrasonic diagnostic apparatus for transmitting an ultrasound signal to a diagnosis target and receiving a reflected ultrasound signal from the diagnosis target to generate an ultrasound image, the ultrasonic diagnostic apparatus comprising:
a display including a screen comprising of plural pixels;
a probe;
a beam former;
a processor connected to the probe and configured to signal-process frame data generated by the beam former to generate ultrasound image data and obtain blood-flow information at plural division positions on the diagnosis target corresponding to respective division regions obtained by dividing an ultrasound image to be displayed on the screen,
wherein each of the division positions is a preset unit of plural pixels on the screen of the display; and
filters configured to filter the ultrasound image data using filtering masks, which are determined corresponding to each of the division positions based on the blood-flow information at each of the division positions, to generate one or more filtered ultrasound image data,
wherein the display is configured to display the ultrasound image on the screen,
wherein the ultrasound image is synthesized by acquiring the divided images corresponding to the respective division position from the respective filtered ultrasound image data and allocating the divided images to the corresponding division regions on the screen, respectively.

2. The apparatus according to claim 1, wherein the processor is configured to set the preset unit of plural pixels according to an input of a user.

3. The apparatus according to claim 1, wherein the processor is configured to convert the ultrasound image from a two-dimensional image to a three-dimensional image.

4. The apparatus according to claim 1, wherein, when the processor sets at least one region of interest (ROI) according to an input of a user, the filters are configured to perform filtering only for the at least one region of interest.

5. The apparatus according to claim 1, wherein the blood-flow information comprises at least one of blood flow-rate information, blood vessel thickness information, blood vessel direction information, blood flow intensity, and blood flow volume.

6. The apparatus according to claim 5, wherein the blood flow rate information is obtained from Doppler information based on the ultrasound signal.

7. The apparatus according to claim 1, wherein:
the ultrasound image to be displayed on the screen is divided into a predetermined number of the division regions each having the same size, and
the processor is configured to set the division positions in correspondence with the division regions, respectively.

8. The apparatus according to claim 7, wherein the processor is configured to set the predetermined number of division regions according to an input of a user.

* * * * *